United States Patent [19]

Spector

[11] Patent Number: 4,523,870
[45] Date of Patent: Jun. 18, 1985

[54] AROMA-DISPENSING CARTRIDGE AND HOLDER ASSEMBLY FOR AUTOMOBILES

[76] Inventor: Donald Spector, 380 Mountain Rd., Union City, N.J. 07087

[21] Appl. No.: 402,031

[22] Filed: Jul. 26, 1982

[51] Int. Cl.$^3$ .............................................. A61L 9/04
[52] U.S. Cl. ..................... 98/2.11; 239/55; 239/57; 239/59
[58] Field of Search ................... 239/53–59; 98/2, 109, 2.11

[56] References Cited

U.S. PATENT DOCUMENTS

| | | | |
|---|---|---|---|
| 170,990 | 12/1875 | Colburn | 98/109 |
| 2,578,827 | 12/1951 | Munnecke | 239/59 |
| 2,763,395 | 9/1956 | Meek | 239/58 |
| 2,797,844 | 7/1957 | Meek | 239/58 |
| 4,220,281 | 9/1980 | Martens et al. | 239/57 |
| 4,374,571 | 2/1983 | Hirvela | 239/56 |

FOREIGN PATENT DOCUMENTS 2060392  5/1981  United Kingdom ................. 239/53

*Primary Examiner*—Andres Kashnikow
*Assistant Examiner*—James R. Moon, Jr
*Attorney, Agent, or Firm*—Michael Ebert

[57] ABSTRACT

An aroma-dispensing cartridge and holder assembly attachable to an air vent in the interior of an automobile. When activated, the assembly functions to diffuse an aromatic vapor into the forced air stream emitted through the vent into the interior. The assembly is constituted by a holder provided with an array of parallel slots and a replaceable cartridge which is telescoped therein. The cartridge contains a porous pad impregnated with a liquid scent and includes a like array of slots. The inserted cartridge is axially shiftable relative to the holder from an inactive position in which the holder and cartridge slots are out of registration to effectively seal the pad, to an active position in which the slots lie in registration, as a consequence of which the forced air stream from the vent passes through the porous pad to volatilize the liquid scent.

5 Claims, 5 Drawing Figures

AROMA-DISPENSING CARTRIDGE AND HOLDER ASSEMBLY FOR AUTOMOBILES

BACKGROUND OF INVENTION

This invention relates generally to aroma dispensers, and in particular to an aroma-dispensing cartridge and holder assembly attachable to an air vent in the interior of an automobile, the assembly when in the active state functioning to diffuse an aromatic vapor into the forced air stream emitted into the interior.

As used herein, the term "aroma" is not limited to pleasant or savory smells but encompasses scents that function as insecticides, air fresheners, deodorants or any other odor that acts to condition, modify or otherwise charge the atmosphere.

The aroma of perfumes and perfume-based products such as colognes and toilet waters was originally derived from the essential oils of plants. However, since the early 19th century, chemists have succeeded in analyzing many essential oils and in creating thousands of synthetics, some simulating natural products and others yielding altogether new scents. Perfumes today are largely blends of natural and synthetic scents and of fixatives which equalize vaporization and enhance pungency. In most liquid scents, the ingredients are combined with alcohol.

Various types of spray devices or dispensers are known for emitting aromas. Thus the patent to Dearling, U.S. Pat. No. 3,330,481, discloses a dispenser for wafting into the atmosphere an insecticide, a pleasant smelling scent or any other aromas, this being accomplished by means of a pressurized container. When the actuating button of this container is pressed, a dispersant is released onto an absorbent material, the absorbent dispersant permeating the atmosphere.

Similarly, the Sekiguchi et al. U.S. Pat. No. 3,679,133 discloses a perfume dispenser which includes a sponge-like head that receives and exudes a charge of perfume. In the spray aerosol can disclosed in the Harrison U.S. Pat. No. 3,972,473, an absorptive ring is impregnated with an air-freshening fragrance and released into the atmosphere. U.S. Pat. Nos. 1,191,821; 3,410,488 and 3,441,353 are along similar lines, for they show wicks and other absorptive materials to accept and emit a perfume or other odoriferous liquid.

While the prior art discloses various embodiments of aroma dispensers, none of these devices is particularly adopted for use in an automotive interior, an environment having special requirements. The atmosphere in most automobiles is somewhat unpleasant, for it is often permeated by exhaust and engine fumes, by odors emanating from the road, and in many cases by tobacco smoke. Hence it becomes desirable to mask or supplant these odors by more agreeable scents.

While a perfume odor may be desirable in a vehicle, since personal tastes differ and the choice of perfume may also depend on other variables, the availability of an aroma dispenser providing a single scent falls short of what is required. Moreover, in some instances the aroma called for is not a perfume but a scent acting as a stimulant to keep the driver awake under driving conditions that may be soporific. Thus the type of pleasing scent that may be appropriate for a morning drive is usually not the same as that suitable for dusk; whereas when driving late at night, what then may be desirable is an odor, which, though perhaps unpleasant, functions to stimulate and awaken rather than relax the driver.

In my prior Pat. No. 4,200,229, there is disclosed an aroma-dispenser mountable under the dashboard of an automobile and taking the form of a replaceable cartridge receivable in a stationary holder so that the user can insert therein whichever cartridge gives off an aroma suitable for a given occasion or satisfying a personal preference. The cartridge, in this instance, includes a bottle containing a liquid scent and a hand-operated suction pump which when actuated serves to spray a liquid scent into the car interior.

An aroma-dispensing assembly of the type disclosed in my prior patent is intermittently effective, for the aromatic liquid is sprayed into the interior only when the pump is actuated, and the duration of the aroma within the interior depends on the lasting power of the particular fragrance used and the degree to which the interior is ventilated. Thus if the car is provided with a forced air circulating ventilation system and this system is in operation, it will function to clear the air of the aroma.

SUMMARY OF INVENTION

Accordingly, the main object of this invention is to provide an aroma-dispensing cartridge and holder assembly for an automobile which cooperates with the forced air ventilation system of the vehicle to diffuse an aromatic vapor into the forced air stream, whereby the aromatically-charged interior atmosphere is continuously maintained as long as the assembly is in its active state.

More particularly, an object of this invention is to provide an assembly of the above type which is readily installable on any air vent in the automobile ventilation system without tools.

Also an object of the invention is to provide an assembly of the above type which may be switched without difficulty from an active condition to an inactive condition.

A significant advantage of an assembly in accordance with the invention is that it makes use of a low cost cartridge having a porous pad therein impregnated with a liquid scent, which cartridge may be disposed of when the scent is exhausted.

Briefly stated, these objects are accomplished in an aroma-dispensing cartridge and holder assembly attachable to an air vent in the interior of an automobile. When activated, the assembly functions to diffuse an aromatic vapor into the forced air stream emitted through the vent into the interior. The assembly is constituted by a holder provided with an array of parallel slots and a replaceable cartridge which is telescoped therein. The cartridge contains a porous pad impregnated with a liquid scent and includes a like array of slots. The inserted cartridge is axially shiftable relative to the holder from an inactive position in which the holder and cartridge slots are out of registration to effectively seal the pad, to an active position in which the slots lie in registration, as a consequence of which the forced air stream from the vent passes through the porous pad to volatilize the liquid scent.

OUTLINE OF DRAWINGS

For a better understanding of the invention as well as other objects and further features thereof, reference is made to the following detailed description to be read in conjunction with the accompanying drawings, wherein.

DESCRIPTION OF INVENTION

Figure 1:
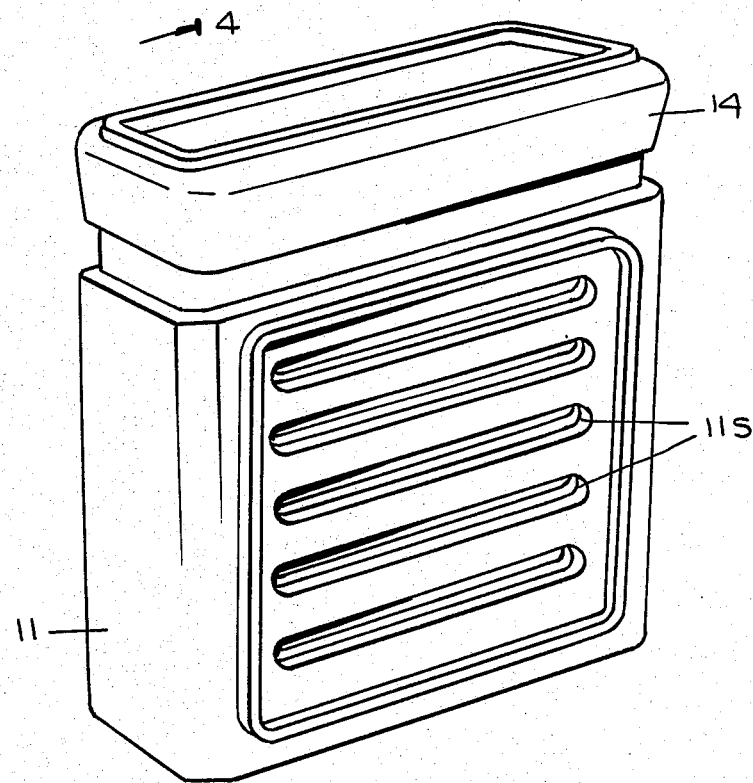
FIG. 1 is a perspective view of an aroma-dispensing holder and cartridge assembly in accordance with the invention, as seen from the front face.

Referring now to the figures of the drawing, there is shown an aroma-dispensing cartridge and holder assembly in accordance with the invention, the assembly consisting of a cartridge generally designated by numeral 10, and a holder, generally designated by numeral 11.

Cartridge 10 is constituted by a receptacle having a box-like form whose front and rear walls are provided with matching arrays of parallel slots 10S. Disposed within the cartridge is a porous pad 13 which may be formed of flexible plastic foam or sponge-like material which is non-reactive with whatever liquid scents are used, or porous paper-like material fabricated of non-woven fibers. The pad is impregnated with an appropriate liquid scent, air freshener or whatever other odoriferous liquid is desired.

The top of cartridge 10 is enclosed by a rectangular cap 14 serving as a handle for the cartridge. In practice, the cap may be labelled to identify the scent carried by the pad housed therein. Thus a user may be supplied with a choice of different fragrances.

Cartridge 10 telescopes within open-topped holder 11 to an extent limited by cap 14 whose rectangular dimensions are somewhat larger than the cross-sectional dimensions of the holder, so that the cap may rest on the upper edge of the holder. Holder 11 is provided at its front and rear walls with matching arrays of parallel slots 11S.

Cartridge 10 is provided on its front and rear walls adjacent the base with a pair of detents 15 which are adapted to selectively nest in a lower set of recesses 16 formed on the inner surfaces of the holder or in a higher set of recesses 17. A flat, compressible spring 18 is interposed between the base of the cartridge and the bottom of the holder to bias the cartridge.

When, therefore, cartridge 14 is pressed down, it acts to compress spring 18 until detents 15 fall into lower recesses 16, this being the inactive state of the assembly. And when cartridge 14 is again pressed to release the detent, the spring urges the cartridge upwardly to cause the detents to fall into the upper recesses 17, at which point the assembly is in its active position. Other well-known mechanical expedients may be used to cause the cartridge to occupy upper and lower positions in the holder.

Figure 4:
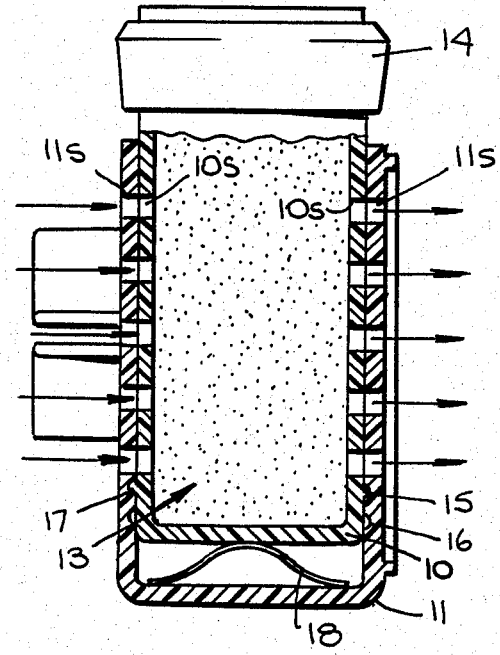
FIG. 4 is a longitudinal section taken through the assembly in its active state.
Figure 2:
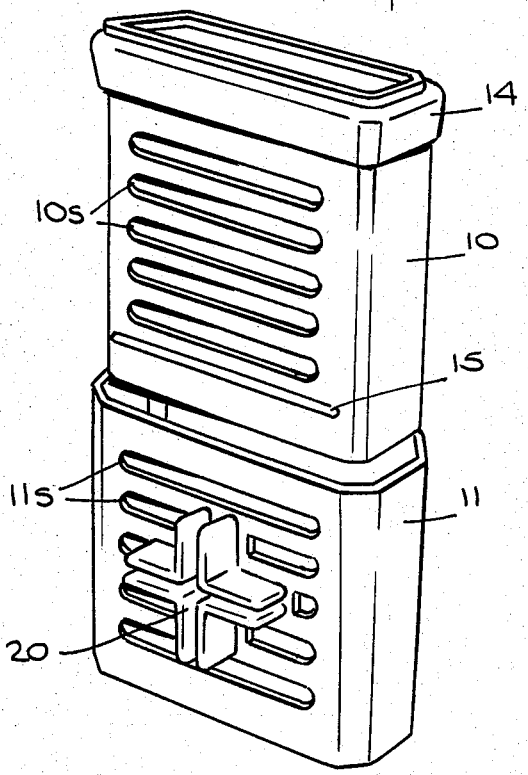
FIG. 2 is a perspective view as seen from the rear face, showing the cartridge removed from its holder.

The active or raised position is shown in FIG. 4, where it will be seen that slots 10S in the cartridge then lie in registration with slots 11S in the holder. The inactive or lowered position is such that these slots are out of registration to effectively seal the pad within the assembly. Thus the slots act as a shutter for the assembly.

Figure 3:
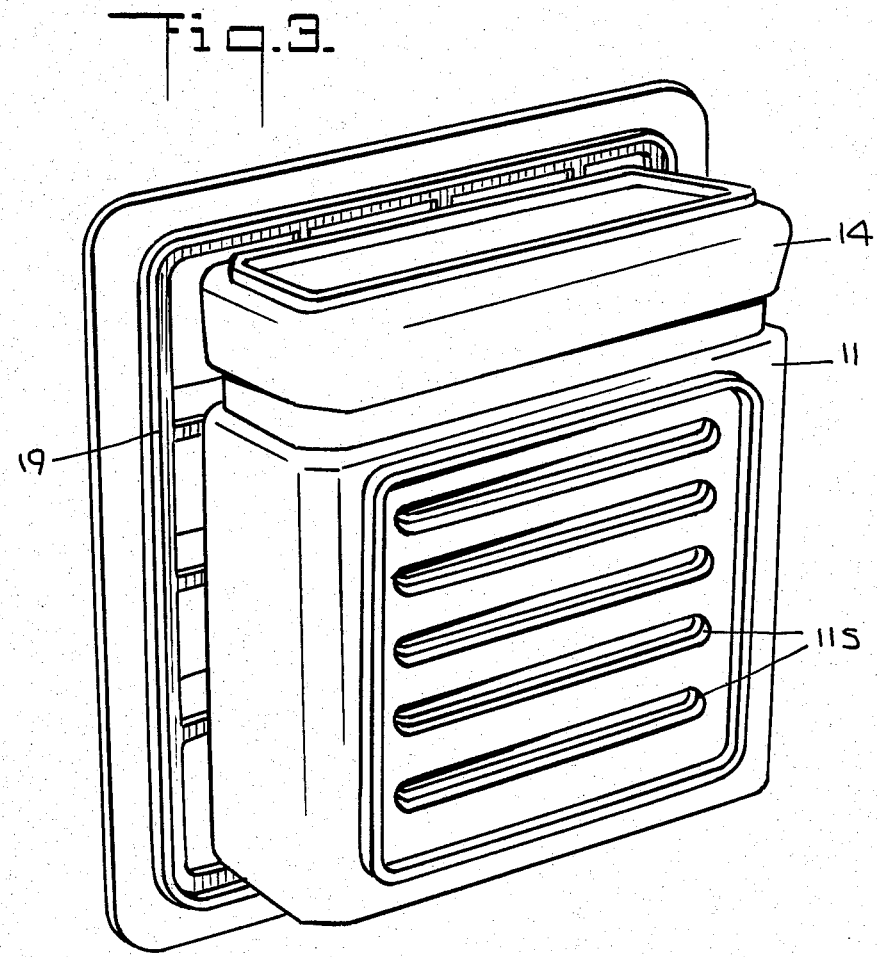
FIG. 3 shows the assembly mounted on the grill of the interior vent of the automobile.
Figure 5:
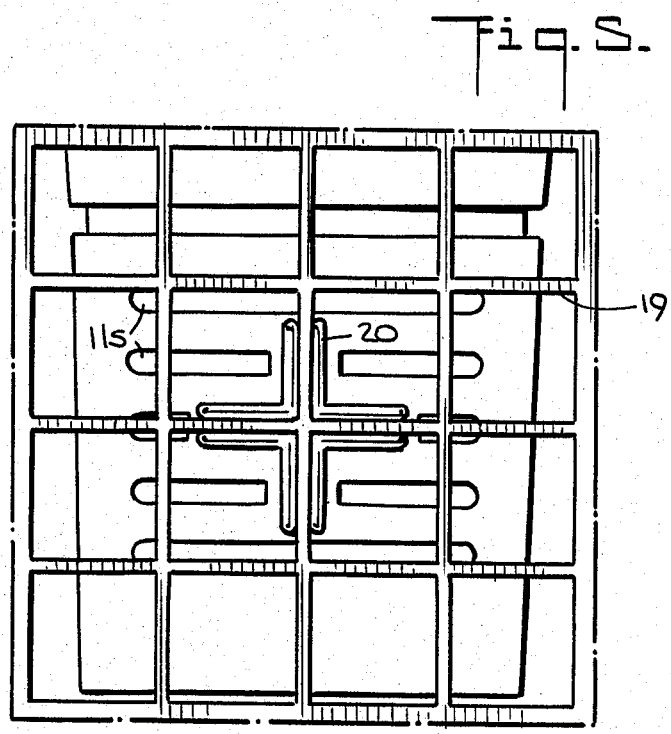
FIG. 5 shows the relationship of the clip of the assembly to the vent grill.

This assembly operates in conjunction with a typical air vent in the interior of the automobile, one such vent 19 being shown in FIG. 3. Several such vents are included in most automotive ventilation systems, forced air being blown therethrough for circulation throughout the car interior. As shown in FIG. 5, the vent is covered by a cellular grill defined by intersecting horizontal or vertical slats.

In order to secure the assembly into the grill, holder 11 is provided on its rear wall with a clip 20 formed by a symmetrical assembly of flexible, right-angle elements in a cruciform formation. The clip, as shown in FIG. 5, is therefore capable of engaging an intersection of the grill slats. In practice, other expedients such as alligator clips may be used to attach the assembly to the vent.

When, therefore, an assembly is mounted over the vent, as shown in FIG. 3, and the assembly is in its active state, the forced air emitted through the vent is then caused to pass through the impregnated pad to volatilize the liquid scent, the resultant aromatic vapor being blown into the car interior. This action is continuous as long as the assembly remains in its activated state. The pad does not, of course, contain an unlimited supply of impregnant; and when the supply is exhausted, the cartridge must be replaced. In practice, however, rather than discard the cartridge when the pad therein is exhausted, the cartridge may be provided with a removable cap, making it possible to withdraw the exhausted pad for re-impregnation with a fresh charge of liquid scent.

While there has been shown and described a preferred embodiment of an aroma-dispensing cartridge and holder assembly for automobiles in accordance with the invention, it will be appreciated that many changes and modifications may be made therein without, however, departing from the essential spirit thereof. Thus, instead of providing a shutter action by shifting the cartridge relative to the holder thereof, the arrangement may be such that the slots in the cartridge are always in registration with those in the holder, and the holder may be provided with a slotted plate which is shiftable relative to the array of slots to provide a shutter action.

Also, while a cruciform clip has been shown which is attachable to a vent at the intersection of the louvres, use may be made of a clip formed by parallel resilient tongs which hold onto the louvres. The invention, though described in conjunction with the vent of an automotive air conditioner, is also usable with any other air conditioner provided with a vent having conditioned air emerging therefrom, the unit diffusing an aroma therein.

I claim:

1. An aroma-dispensing system comprising a cartridge and holder assembly which when activated functions to diffuse an aromatic vapor into a forced air stream intercepted by the assembly, said assembly operating in combination with means in which said stream is emitted through a vent grill formed by at least one slat, said assembly comprising:
  A. an open-top holder having a rectangular cross section, the front and rear walls thereof having corresponding arrays of parallel slots, said holder being provided at its rear wall with releasable clip means provided with a pair of cooperating flexible elements engaging the slat of the grill to secure the assembly thereto, whereby the forced air therefrom is intercepted by the assembly;
  B. a cartridge telescopically receivable in the holder and having front and rear walls provided with similar arrays of parallel slots, said cartridge housing a pad of porous material permeable to said forced air stream and impregnated with a liquid scent; and C. control means to render said cartridge axially shiftable relative to the holder from an active position in which the holder and cartridge slots lie in registration, thereby permitting the forced air stream to pass through the pad to volatilize the liquid to produce said aromatic vapor, to an inactive position in which the slots are out of registration to effectively seal the cartridge.

2. An assembly as set forth in claim 1, wherein said pad is formed of flexible foam plastic material.

3. An assembly as set forth in claim 1, wherein said cartridge is provided with a rectangular cap which in the inactive position rests on the top edge of the holder.

4. An assembly as set forth in claim 3, wherein said cap is removable to permit replacement of the pad.

5. An assembly as set forth in claim 1, wherein said control means include a detent to retain said holder at either the active or inactive position.

* * * * *